(12) United States Patent
Bossolo et al.

(10) Patent No.: US 12,247,111 B2
(45) Date of Patent: Mar. 11, 2025

(54) FLUOROELASTOMER COMPOSITION

(71) Applicant: SOLVAY SPECIALTY POLYMERS ITALY S.P.A., Bollate (IT)

(72) Inventors: Stefano Bossolo, Parabiago (IT); Matteo Fantoni, Vanzaghello (IT); Margherita Albano, Milan (IT)

(73) Assignee: SOLVAY SPECIALTY POLYMERS ITALY S.P.A., Bollate (IT)

( * ) Notice: Subject to any disclaimer, the term of this patent is extended or adjusted under 35 U.S.C. 154(b) by 615 days.

(21) Appl. No.: 17/435,514

(22) PCT Filed: Mar. 25, 2020

(86) PCT No.: PCT/EP2020/058435
§ 371 (c)(1),
(2) Date: Sep. 1, 2021

(87) PCT Pub. No.: WO2020/188125
PCT Pub. Date: Sep. 24, 2020

(65) Prior Publication Data
US 2022/0135774 A1    May 5, 2022

(30) Foreign Application Priority Data
Mar. 20, 2019 (EP) .................... 19163926

(51) Int. Cl.
| | |
|---|---|
| C08K 13/02 | (2006.01) |
| C07C 303/22 | (2006.01) |
| C07D 213/127 | (2006.01) |
| C08F 214/28 | (2006.01) |
| C08K 3/04 | (2006.01) |
| C08K 3/22 | (2006.01) |
| C08K 5/136 | (2006.01) |
| C08K 5/42 | (2006.01) |
| C08K 5/5399 | (2006.01) |

(52) U.S. Cl.
CPC ............ *C08K 13/02* (2013.01); *C07C 303/22* (2013.01); *C07D 213/127* (2013.01); *C08F 214/282* (2013.01); *C08K 3/04* (2013.01); *C08K 3/22* (2013.01); *C08K 2003/222* (2013.01); *C08K 5/136* (2013.01); *C08K 5/42* (2013.01); *C08K 5/5399* (2013.01)

(58) Field of Classification Search
CPC .... C08K 13/02; C08F 214/22; C07D 213/127
See application file for complete search history.

(56) References Cited

U.S. PATENT DOCUMENTS

| | | |
|---|---|---|
| 3,752,787 A | 8/1973 | De Brunner |
| 3,876,654 A | 4/1975 | Pattison |
| 4,233,427 A | 11/1980 | Bargain et al. |
| 4,259,463 A | 3/1981 | Moggi et al. |
| 4,734,460 A | 3/1988 | Yamada |
| 4,734,465 A * | 3/1988 | Moggi ............ C08F 8/00 525/326.3 |
| 2018/0142050 A1* | 5/2018 | Fantoni ............ C08K 5/0025 |

FOREIGN PATENT DOCUMENTS

| | | |
|---|---|---|
| EP | 120462 A1 | 10/1984 |
| EP | 182299 A2 | 5/1986 |
| EP | 335705 A1 | 10/1989 |
| EP | 661304 A1 | 7/1995 |
| EP | 684277 A1 | 11/1995 |
| WO | 2016180660 A1 | 11/2016 |

* cited by examiner

*Primary Examiner* — Wenwen Cai
(74) *Attorney, Agent, or Firm* — Osha Bergman Watanabe & Burton LLP

(57) ABSTRACT

The invention pertains to a fluoroelastomer composition comprising a vinylidene-fluoride based fluoroelastomer, a polyhydroxylated compound, a basic compound, a pyridinium-type salt having an aromatic ring-quaternized nitrogen atom, and comprising at least two groups having a central carbon atom which bears acidic hydrogen atoms; and an accelerant, which possesses an improved molding behaviour, leading to shaped parts possessing less blisters and surface defects.

14 Claims, No Drawings

FLUOROELASTOMER COMPOSITION

CROSS-REFERENCE TO RELATED APPLICATION

This application is a U.S. national stage entry under 35 U.S.C. § 371 of International Application No. PCT/EP2020/058435 filed Mar. 25, 2020, which claims priority to European Application No. 19163926.9, filed on Mar. 20, 2019. The entire contents of these applications are explicitly incorporated herein by this reference.

TECHNICAL FIELD

The invention relates to a fluoroelastomer curable composition, to a method for curing the same, and to cured articles derived there from.

BACKGROUND ART

Vulcanized fluoroelastomers have been used in a variety of applications, in particular for manufacturing sealing articles such as oil seals, gaskets, shaft seals and O-rings, because of several desirable properties such as heat resistance, chemical resistance, weatherability, etc.

It is nevertheless required for "as polymerized" fluoroelastomers to undergo curing/crosslinking processes (so-called "vulcanization") in order to ensure required sealing and mechanical properties to be exhibited in final parts.

Several techniques have been developed for ensuring creation of a three-dimensional cured structure able to deliver expected performances; the underlying chemistry generally requires a crosslinking agent to provide for connections between fluoroelastomer polymer chains. Ionic curing systems are based on polyhydroxyaromatic compounds (typically bi-phenols), reacting through "ionic" chemistry in the presence of basic compounds and onium accelerators, via displacement of acidic hydrogen atoms in the chain.

An example of an ionically curable compound is described in U.S. Pat. No. 4,734,460 (NIPPON MEKTRON) 29 Mar. 1988, which discloses certain compositions including a fluoroelastomer, an oxide or hydroxide of a divalent metal, a polyhydroxyaromatic compound, and a quaternary ammonium salt of formula:

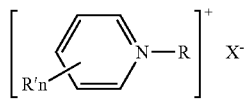

with R being an aralkyl group, R' being an alkyl, aryl or aralkyl group, n being 1 to 5 and X being an anion, to be used in an amount of 0.1 to 10 phr, preferably 0.1 to 2 phr. In a long list of possible onium salts, is mention made of 1-benzyl-2,4,6-trimethylpyridinium chloride.

Recently, WO 2016/180660 A (SOLVAY SPECIALTY POLYMERS ITALY SPA) 17 Nov. 2016 has proposed a novel curing system as an alternative to ionic curing, relying on the reactivity of certain pyridinium-type salts possessing reactive hydrogen atoms on at least two groups in ortho or para position with respect to the ring-quaternized pyridinium-type nitrogen.

For fluoroelastomers to be fully accepted for automated molding, the ability to be processed and cured with as low as possible of failing parts, blisters on the surface, and/or exaggerated flashes at boundaries, and/or with minimum post-processing for removing flashes or other imperfections.

There is hence a continuous quest in this domain for fluororubber solutions possessing improved injection molding behaviour, in particular, less blisters and flashes in molded parts, when increasing injection molding processing rates.

SUMMARY OF INVENTION

The Applicant has now found that certain fluoroelastomer formulations can be injection molded and cured through the combined action of certain pyridinium-type salts and certain ionic curing ingredients delivering improved processability, and enabling manufacturing of parts with less blisters and flashes at high manufacture speed.

It is hence a first object of the present invention a fluoroelastomer composition [composition (C)] comprising:
- at least one vinylidene-fluoride based fluoroelastomer comprising recurring units derived from vinylidene fluoride (VDF) and from at least one additional (per) fluorinated monomer different from VDF [fluoroelastomer (A)];
- at least one polyhydroxylated compound [compound (OH)];
- at least one basic compound [base (B)];
- at least one pyridinium-type salt [salt (P)] having an aromatic ring-quaternized nitrogen atom, and comprising at least two groups [groups (alpha-H)] having a central carbon atom which bears at least a hydrogen atom and which is covalently bound to a $sp^2$-hybridized carbon of an annular aromatic carbon which is in ortho or para position to the said aromatic ring-quaternized nitrogen atom;
- at least one accelerant [accelerant (A)], different from salt (P), selected from the group consisting of organic P, As, Se or S-onium compound, amino-phosphonium derivatives, phosphoranes, and diphosphine-iminium compounds.

The Applicant has surprisingly found that when combining ionic curing involving polyhydroxylated compound, base and accelerants, with salts (P) including a ring-quaternized pyridinium-type nitrogen, and possessing at least two groups in ortho or para position with respect to the said ring-quaternized pyridinium-type nitrogen comprising reactive hydrogen atoms, molding and cross-linking in the presence of the said mixed crosslinking system has been proven to proceed in improved manner, with excellent molding and demolding performances, with high yield and substantially no mold fouling, significantly reduced blisters and flashes, in conventional equipments.

Without being bound by this theory, the Applicant believes that this is an effect of the double crosslinking mechanisms, through both polyhydroxylated compounds, and hence ionic bonding through O-atoms, and salts (P), and hence ionic bonding through C-atoms. Indeed, salts (P) bear hydrogen atoms in their groups (alpha-H) which possess suitable reactivity to generate, under curing conditions, corresponding carbanions, while polyhydroxylated compounds are known to provide for corresponding "phenolate"/"alcholate"-type oxy-anions under same conditions, both the so formed carbanions and oxy-anions having sufficient reactivity/nucleophilic character to ensure activation and grafting of the fluoroelastomer polymer chain.

It is hence critical for salt (P) to include the said groups (alpha-H) in ortho or para positions with respect to the quaternized nitrogen atoms: compounds similar to salts (P), but either possessing only one group (alpha-H) in ortho or para position or possessing said groups (alpha-H) in meta position are not effective. Examples of compounds which fails to possess at least two groups in ortho or para position with respect to a ring-quaternized pyridinium-type nitrogen, hence different from salts (P), and which are ineffective, are those of formulae (Ex-10c) to (Ex-13c):

(Ex-10c)

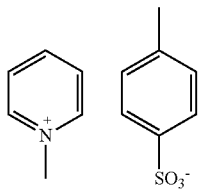

(Ex-11c)

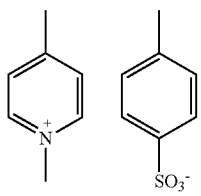

(Ex-12c)

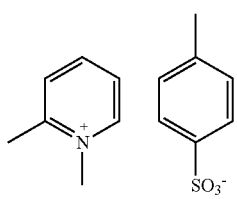

(Ex-13c)

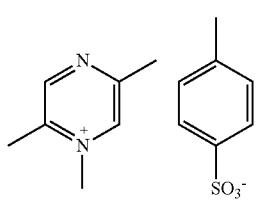

DESCRIPTION OF INVENTION

For the purposes of this invention, the term "fluoroelastomer" [fluoroelastomer (A)] is intended to designate a fluoropolymer resin serving as a base constituent for obtaining a true elastomer, said fluoropolymer resin comprising more than 10% wt, preferably more than 30% wt, of recurring units derived from at least one ethylenically unsaturated monomer comprising at least one fluorine atom (hereafter, (per)fluorinated monomer) and, optionally, recurring units derived from at least one ethylenically unsaturated monomer free from fluorine atom (hereafter, hydrogenated monomer).

True elastomers are defined by the ASTM, Special Technical Bulletin, No. 184 standard as materials capable of being stretched, at room temperature, to twice their intrinsic length and which, once they have been released after holding them under tension for 5 minutes, return to within 10% of their initial length in the same time.

Fluoroelastomers (A) are in general amorphous products or products having a low degree of crystallinity (crystalline phase less than 20% by volume) and a glass transition temperature ($T_g$) below room temperature. In most cases, the fluoroelastomer (A) has advantageously a $T_g$ below 10° C., preferably below 5° C., more preferably 0° C., even more preferably below −5° C.

Fluoroelastomer (A) typically comprises at least 15% moles, preferably at least 20% moles, more preferably at least 35% moles of recurring units derived from VDF, with respect to all recurring units of the fluoroelastomer.

Fluoroelastomer (A) typically comprises at most 85% moles, preferably at most 80% moles, more preferably at most 78% moles of recurring units derived from VDF, with respect to all recurring units of the fluoroelastomer.

Non limitative examples of suitable (per)fluorinated monomers, recurring units derived therefrom being comprised in the fluoroelastomer (A), are notably:

(a) $C_2$-$C_8$ perfluoroolefins, such as tetrafluoroethylene (TFE) and hexafluoropropylene (HFP);
(b) hydrogen-containing $C_2$-$C_8$ olefins different from VDF, such as vinyl fluoride (VF), trifluoroethylene (TrFE), perfluoroalkyl ethylenes of formula $CH_2=CH—R_f$, wherein $R_f$ is a $C_1$-$C_6$ perfluoroalkyl group;
(c) $C_2$-$C_8$ chloro and/or bromo and/or iodo-fluoroolefins such as chlorotrifluoroethylene (CTFE);
(d) (per)fluoroalkylvinylethers (PAVE) of formula $CF_2=CFOR_f$, wherein $R_f$ is a $C_1$-$C_6$ (per)fluoroalkyl group, e.g. $CF_3$, $C_2F_5$, $C_3F_7$;
(e) (per)fluoro-oxy-alkylvinylethers of formula $CF_2=CFOX$, wherein X is a $C_1$-$C_{12}$ ((per)fluoro)-oxyalkyl comprising catenary oxygen atoms, e.g. the perfluoro-2-propoxypropyl group;
(f) (per)fluorodioxoles having formula:

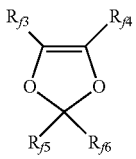

wherein each of $R_{f3}$, $R_{f4}$, $R_{f5}$, $R_{f6}$, equal or different each other, is independently a fluorine atom, a $C_1$-$C_6$ fluoro- or per(halo)fluoroalkyl, optionally comprising one or more oxygen atom, e.g. —$CF_3$, —$C_2F_5$, —$C_3F_7$, —$OCF_3$, —$OCF_2CF_2OCF_3$.

(g) (per)fluoro-methoxy-vinylethers (MOVE, hereinafter) having formula: $CFX_2=CX_2OCF_2OR''_f$
wherein $R''_f$ is selected among $C_1$-$C_6$ (per)fluoroalkyls, linear or branched; $C_5$-$C_6$ cyclic (per)fluoroalkyls; and $C_2$-$C_6$ (per)fluorooxyalkyls, linear or branched, comprising from 1 to 3 catenary oxygen atoms, and $X_2=F$, H; preferably $X_2$ is F and $R''_f$ is —$CF_2CF_3$ (MOVE1); —$CF_2CF_2OCF_3$ (MOVE2); or —$CF_3$ (MOVE3).

Generally fluoroelastomer (A) will comprise recurring units derived from VDF and recurring units derived from HFP.

Fluoroelastomer (A) may optionally further comprise recurring units derived from one or more than one monomer free from fluorine (hydrogenated monomer, herein after). Examples of hydrogenated monomers are notably $C_2$-$C_8$ non-fluorinated olefins (OI), in particular $C_2$-$C_8$ non-fluorinated alpha-olefins (OI), including ethylene, propylene, 1-butene; diene monomers; styrene monomers; $C_2$-$C_8$ non-fluorinated alpha-olefins (OI), and more particularly ethylene and propylene, will be selected for achieving increased resistance to bases.

Optionally, fluoroelastomer (A) may comprises recurring units derived from at least one bis-olefin [bis-olefin (OF)] having general formula:

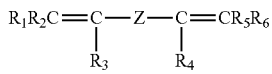

wherein $R_1$, $R_2$, $R_3$, $R_4$, $R_5$ and $R_6$, equal or different from each other, are H, a halogen, or a $C_1$-$C_5$ optionally halogenated group, possibly comprising one or more oxygen group; Z is a linear or branched $C_1$-$C_{18}$ optionally halogenated alkylene or cycloalkylene radical, optionally containing oxygen atoms, or a (per)fluoropolyoxyalkylene radical, e.g. as described in EP 661304 A (AUSIMONT SPA) 5 Jul. 1995.

The bis-olefin (OF) is preferably selected from the group consisting of those complying with formulae (OF-1), (OF-2) and (OF-3):
(OF-1)

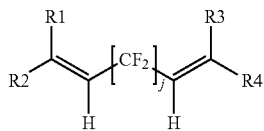

wherein j is an integer between 2 and 10, preferably between 4 and 8, and $R_1$, $R_2$, $R_3$, $R_4$, equal or different from each other, are H, F or $C_{1-5}$ alkyl or (per)fluoroalkyl group;
(OF-2)

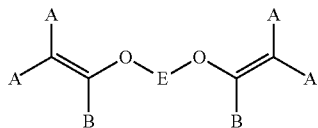

wherein each of A, equal or different from each other and at each occurrence, is independently selected from F, Cl, and H; each of B, equal or different from each other and at each occurrence, is independently selected from F, Cl, H and $OR_B$, wherein $R_B$ is a branched or straight chain alkyl radical which can be partially, substantially or completely fluorinated or chlorinated; E is a divalent group having 2 to 10 carbon atom, optionally fluorinated, which may be inserted with ether linkages; preferably E is a —$(CF_2)_m$— group, with m being an integer from 3 to 5; a preferred bis-olefin of (OF-2) type is $F_2C=CF—O—(CF_2)_5—O—CF=CF_2$.
(OF-3)

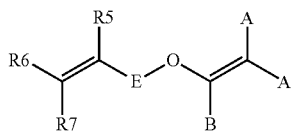

wherein E, A and B have the same meaning as above defined; R5, R6, R7, equal or different from each other, are H, F or $C_{1-5}$ alkyl or (per)fluoroalkyl group.

Fluoroelastomers (A) suitable in the compositions of the invention may comprise, in addition to recurring units derived from VDF and HFP, one or more of the followings:
- recurring units derived from at least one bis-olefin [bis-olefin (OF)] as above detailed;
- recurring units derived from at least one (per)fluorinated monomer different from VDF and HFP; and
- recurring units derived from at least one hydrogenated monomer.

Among specific monomer compositions of fluoroelastomers (A) suitable for the purpose of the invention, mention can be made of fluoroelastomers having the following monomer compositions (in mol %):

(i) vinylidene fluoride (VDF) 35-85%, hexafluoropropene (HFP) 10-45%, tetrafluoroethylene (TFE) 0-30%, perfluoroalkyl vinyl ethers (PAVE) 0-15%, bis-olefin (OF) 0-5%;

(ii) vinylidene fluoride (VDF) 50-80%, perfluoroalkyl vinyl ethers (PAVE) 5-50%, tetrafluoroethylene (TFE) 0-20%, bis-olefin (OF) 0-5%;

(iii) vinylidene fluoride (VDF) 20-30%, $C_2$-$C_8$ non-fluorinated olefins (OI) 10-30%, hexafluoropropene (HFP) and/or perfluoroalkyl vinyl ethers (PAVE) 18-27%, tetrafluoroethylene (TFE) 10-30%, bis-olefin (OF) 0-5%;

(vii) tetrafluoroethylene (TFE) 33-75%, perfluoroalkyl vinyl ethers (PAVE) 15-45%, vinylidene fluoride (VDF) 5-30%, hexafluoropropene HFP 0-30%, bis-olefin (OF) 0-5%;

(viii) vinylidene fluoride (VDF) 35-85%, fluorovinyl ethers (MOVE) 5-40%, perfluoroalkyl vinyl ethers (PAVE) 0-30%, tetrafluoroethylene (TFE) 0-40%, hexafluoropropene (HFP) 0-30%, bis-olefin (OF) 0-5%.

As said, composition (C) comprises at least one salt (P), as detailed above. Generally, salt (P) is selected from the group consisting of compounds complying with any of formulae (P1) to (12):

(P-1)
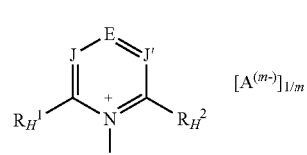

(P-2)
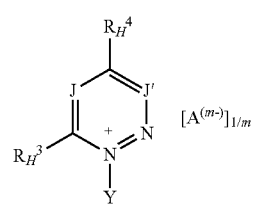

(P-3)
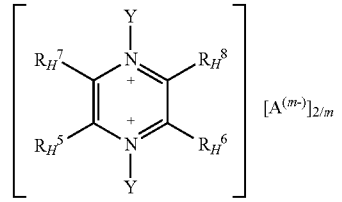

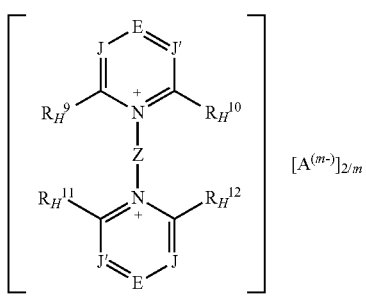
(P-4)

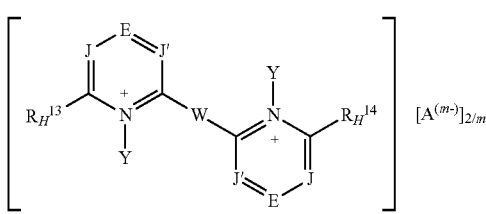
(P-5)

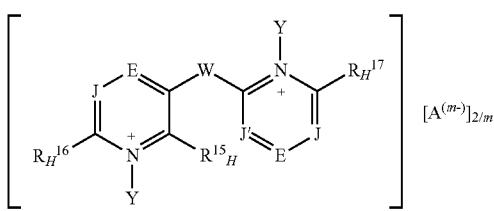
(P-6)

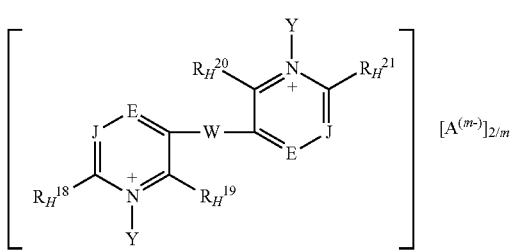
(P-7)

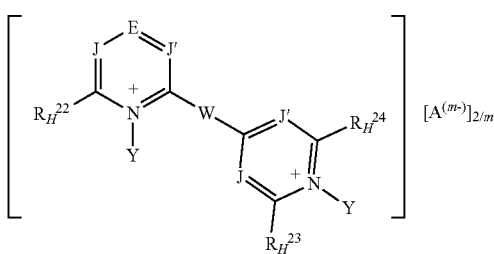
(P-8)

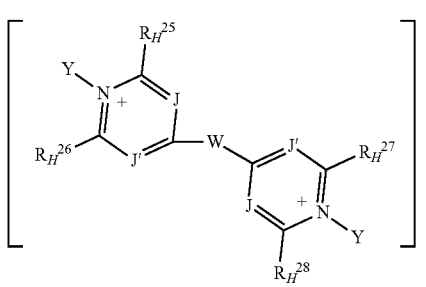
(P-9)

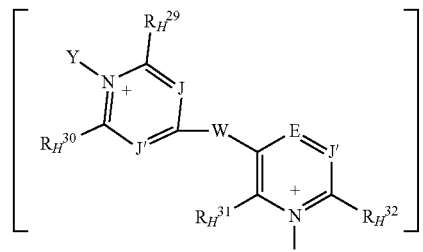
(P-10)

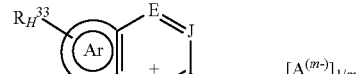
(P-11)

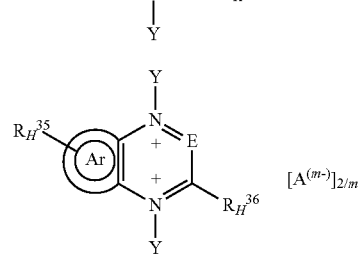
(P-12)

wherein:

each of J and J', equal to or different from each other, is independently at each occurrence C—R* or N, wherein R* is H or a $C_1$-$C_{12}$ hydrocarbon group;

E is N or a group of formula C—R°$_H$;

Z is a divalent hydrocarbon group comprising from 1 to 12 carbon atoms;

W is a bond or is a bridging group selected from the group consisting of divalent hydrocarbon groups comprising from 1 to 12 carbon atoms (preferably divalent aliphatic groups comprising from 1 to 6 carbon atoms) and divalent fluorocarbon groups comprising from 1 to 12 carbon atoms (preferably divalent perfluoroaliphatic groups comprising from 1 to 6 carbon atoms);

the group sketched with symbol:

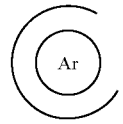

in formula (P-11) and (P-12) designates an aromatic mono- or poly-nuclear ring condensed to the pyridinium-type aromatic ring, which may comprise one or more additional nitrogen atoms, optionally quaternized nitrogen atoms, in the ring(s);

each of $R^1_H$, $R^2_H$, $R^3_H$, $R^4_H$, $R^5_H$, $R^6_H$, $R^7_H$, $R^8_H$, $R^9_H$, $R^{10}_H$, $R^{11}_H$, $R^{12}_H$, $R^{13}_H$, $R^{14}_H$, $R^{15}_H$, $R^{16}_H$, $R^{17}_H$, $R^{18}_H$, $R^{19}_H$, $R^{20}_H$, $R^{21}_H$, $R^{22}_H$, $R^{23}_H$, $R^{24}_H$, $R^{25}_H$, $R^{26}_H$, $R^{27}_H$, $R^{28}_H$, $R^{29}_H$, $R^{30}_H$, $R^{31}_H$, $R^{32}_H$, $R^{33}_H$, $R^{34}_H$, $R^{35}_H$, $R^{36}_H$ and R°$_H$, equal to or different from each other, is independently at each occurrence —H or a group of formula [group (alpha-H)]:

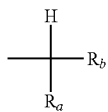

wherein $R_a$, and $R_b$, equal to or different from each other, are independently H or a hydrocarbon $C_1$-$C_6$ group;

Y, equal to or different from each other, is independently oxygen or a $C_1$-$C_{12}$ hydrocarbon group, which can be notably an aliphatic or an aromatic group, which can comprise one or more than one heteroatoms selected from N, O, S and halogens;

$A^{(m-)}$ is an anion having valency m;

with the provisio that (i) when salt (P) is of formula (P-1) at least two of $R^1{}_H$, $R^2{}_H$, and $R^o{}_H$ are groups (alpha-H);

(ii) when salt (P) is of formula (P-2) $R^3{}_H$ and $R^4{}_H$ are groups (alpha-H);

(iii) when salt (P) is of formula (P-3), at least two of $R^5{}_H$, $R^6{}_H$, $R^7{}_H$, and $R^8{}_H$ are groups (alpha-H);

(iv) when salt (P) is of formula (P-4), at least two of $R^9{}_H$, $R^{10}{}_H$, $R^{11}{}_H$, $R^{12}{}_H$, and $R^o{}_H$ are groups (alpha-H);

(v) when salt (P) is of formula (P-5), at least two of $R^{13}{}_H$, $R^{14}{}_H$, and $R^o{}_H$ are groups (alpha-H);

(vi) when salt (P) is of formula (P-6), at least two of $R^{15}{}_H$, $R^{16}{}_H$, $R^{17}{}_H$, and $R^o{}_H$ are groups (alpha-H);

(vii) when salt (P) is of formula (P-7), at least two of $R^{18}{}_H$, $R^{19}{}_H$, $R^{20}{}_H$, $R^{21}{}_H$, and $R^o{}_H$ are groups (alpha-H);

(viii) when salt (P) is of formula (P-8), at least two of $R^{22}{}_H$, $R^{23}{}_H$, $R^{24}{}_H$, and $R^o{}_H$ are groups (alpha-H);

(ix) when salt (P) is of formula (P-9), at least two of $R^{25}{}_H$, $R^{26}{}_H$, $R^{27}{}_H$, and $R^{28}{}_H$ are groups (alpha-H);

(x) when salt (P) is of formula (P-10), at least two of $R^{29}{}_H$, $R^{30}{}_H$, $R^{31}{}_H$, $R^{32}{}_H$, and $R^{28}{}_H$ are groups (alpha-H);

(xi) when salt (P) is of formula (P-11), at least two of $R^{33}{}_H$, $R^{34}{}_H$, and $R^{28}{}_H$ are groups (alpha-H);

(xii) when salt (P) is of formula (P-12), at least two of $R^{35}{}_H$, $R^{36}{}_H$ and $R^o{}_H$ are groups (alpha-H), and at least one accelerant Preferred salts (P) of formula (P-1) are those complying with formulae (P-1-a) to (P-1-e):

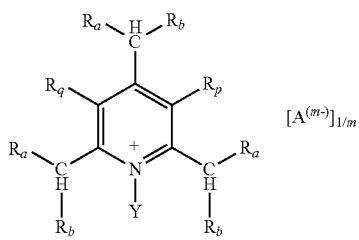

(P-1-a)

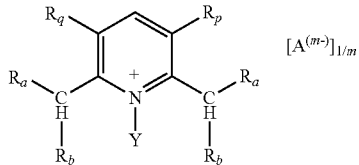

(P-1-b)

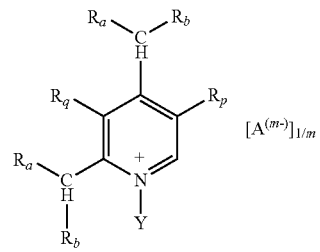

(P-1-c)

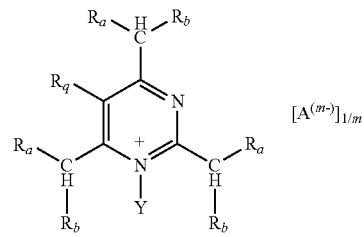

(P-1-d)

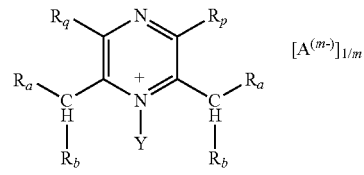

(P-1-e)

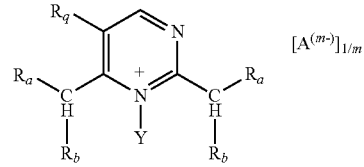

(P-1-f)

wherein:

$R_a$ and $R_b$ have the meaning as above defined, preferably $R_a$ and $R_b$ are H;

Y has the meaning as defined above, preferably Y is methyl;

each of $R_p$ and $R_q$, equal to or different from each other, is H or a $C_1$-$C_{12}$ hydrocarbon group;

A and m have the meanings as above defined.

More preferably, salts (P) of formula (P-1) are those having any of formulae (P-1-g) to (P-1-p):

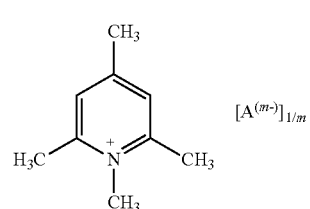

(P-1-g)

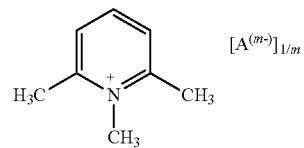

(P-1-h)

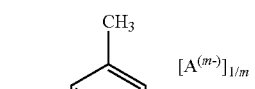 (P-1-i)

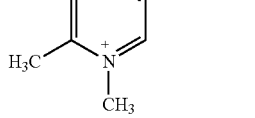 (P-1-l)

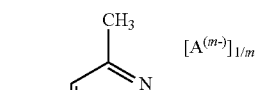 (P-1-m)

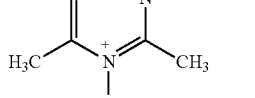 (P-1-n)

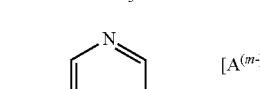 (P-1-o)

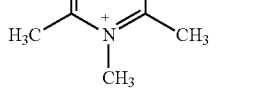 (P-1-p)

wherein A and m have the meaning as above detailed.

Preferred salts (P) of formula (P-2) are those complying with formula (P-2-a):

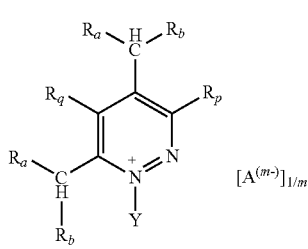 (P-2-a)

wherein:

$R_a$ and $R_b$ have the meaning as above defined, preferably $R_a$ and $R_b$ are H;

Y has the meaning as defined above, preferably Y is methyl;

each of $R_p$ and $R_q$, equal to or different from each other, is H or a $C_1$-$C_{12}$ hydrocarbon group;

A and m have the meanings as above defined.

More preferably, salts (P) of formula (P-2) are those having formula (P-2-b)

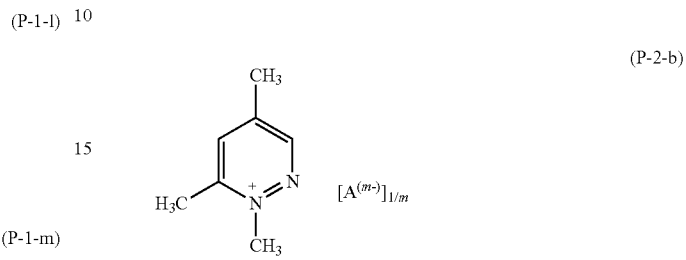 (P-2-b)

wherein A and m have the meaning as above detailed.

Preferred salts (P) of formula (P-3) are those complying with formula (P-3-a):

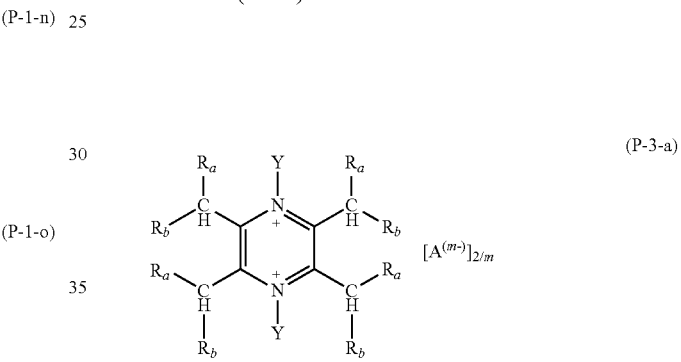 (P-3-a)

wherein:

$R_a$ and $R_b$ have the meaning as above defined, preferably $R_a$ and $R_b$ are H;

Y has the meaning as defined above, preferably Y is methyl;

A and m have the meanings as above defined.

More preferably, salts (P) of formula (P-3) are those having formula (P-3-b)

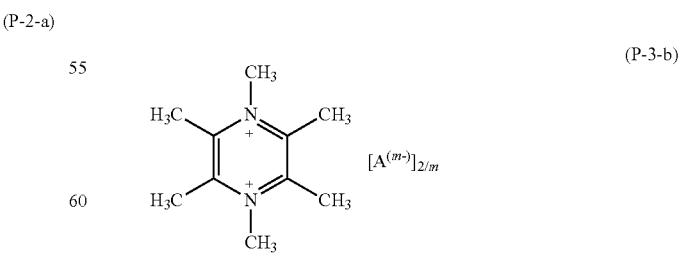 (P-3-b)

wherein A and m have the meaning as above detailed.

Preferred salts (P) of formula (P-4) are those complying with formula (P-4-a):

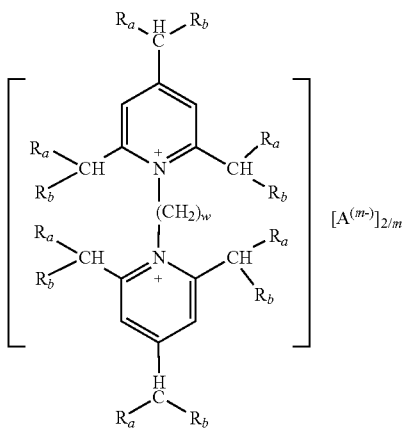

(P-4-a)

wherein:

$R_a$ and $R_b$ have the meaning as above defined, preferably $R_a$ and $R_b$ are H;

w is an integer of 1 to 12, preferably of 1 to 6, most preferably equal to 3;

A and m have the meanings as above defined.

More preferably, salts (P) of formula (P-4) are those having formula (P-4-b) or (P-4-c):

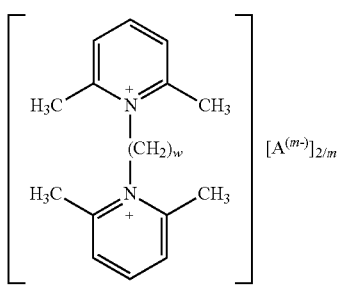

(P-4-b)

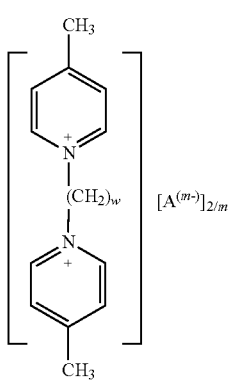

(P-4-c)

wherein A, and m have the meaning as above detailed, and w=3.

Preferred salts (P) of formula (P-5) are those complying with formula (P-5-a):

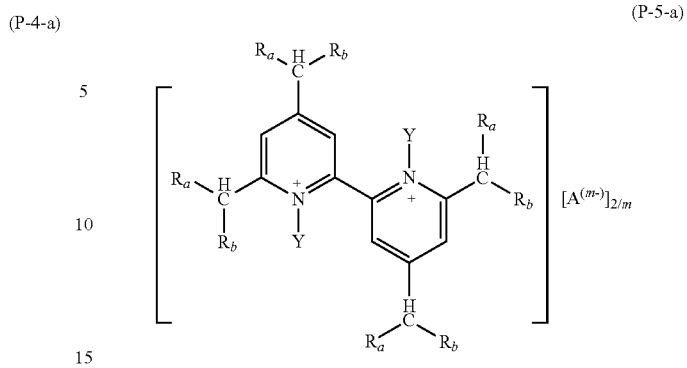

(P-5-a)

wherein:

$R_a$ and $R_b$ have the meaning as above defined, preferably $R_a$ and $R_b$ are H;

Y has the meaning as defined above, preferably Y is methyl;

A and m have the meanings as above defined.

More preferably, salts (P) of formula (P-5) are those having formula (P-5-b) or (P-5-c):

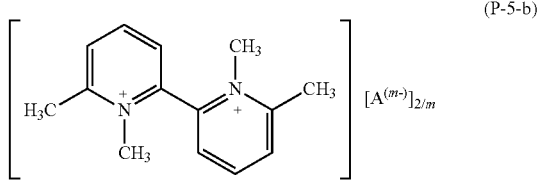

(P-5-b)

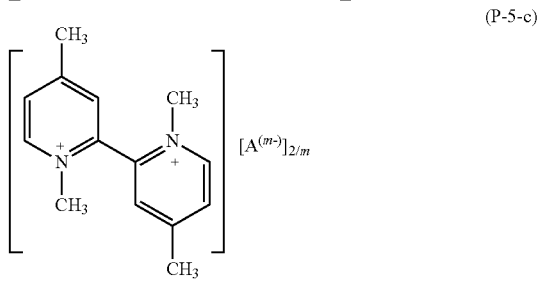

(P-5-c)

wherein A and m have the meaning as above detailed.

Preferred salts (P) of formula (P-11) are those complying with formula (P-11-a):

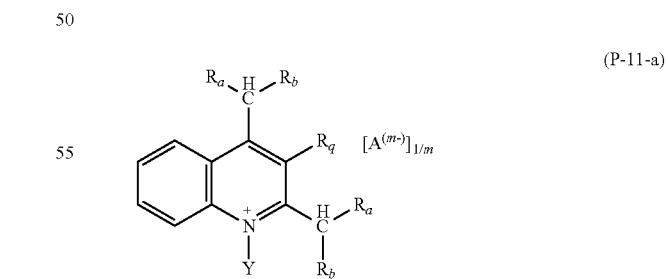

(P-11-a)

wherein:

$R_a$ and $R_b$ have the meaning as above defined, preferably $R_a$ and $R_b$ are H;

Y has the meaning as defined above, preferably Y is methyl;

A and m have the meanings as above defined.

More preferably, salts (P) of formula (P-11) are those having formula (P-11-b):

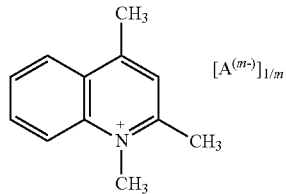
(P-11-b)

wherein A and m have the meaning as above detailed.

Preferred salts (P) of formula (P-12) are those complying with formula (P-12-a):

(P-12-a)

wherein:
- $R_a$ and $R_b$ have the meaning as above defined, preferably $R_a$ and $R_b$ are H;
- Y has the meaning as defined above, preferably Y is methyl;
- A and m have the meanings as above defined.

More preferably, salts (P) of formula (P-12) are those having formula (P-12-b):

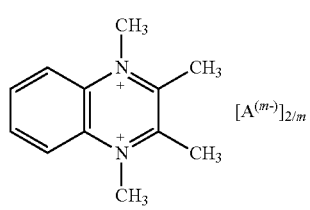
(P-12-b)

wherein A and m have the meaning as above detailed.

The choice of the anion A in formulae (P-1) to (P-12) is not particularly critical; it is nevertheless understood that anions selected from the group consisting of arylsulfonates, in particular, tosylate (p-toluensulfonate), (fluoro)alkyl sulfonates having a $C_1$-$C_6$ (fluoro)alkyl chain, including fluorine-free alkyl sulfonates e.g. mesylate (methansulfonate) and fluorine containing (especially perfluorinated) alkyl sulfonates, e.g. triflate (trifluoromethansulfonate); halides (iodide, bromide, chloride) may be particularly preferred because of their prompt accessibility from synthetic perspective.

As a whole, exemplary compounds which have been found particular utility in the composition of the present invention are those listed below having formulae (Ex-1) to (Ex-9):

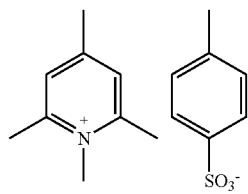
(Ex-1)

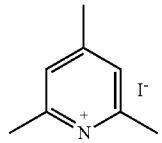
(Ex-2)

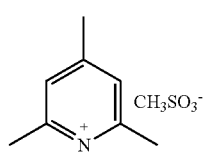
(Ex-3)

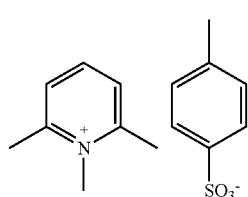
(Ex-4)

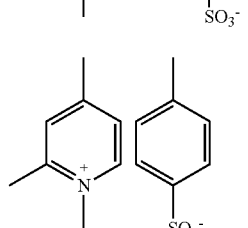
(Ex-5)

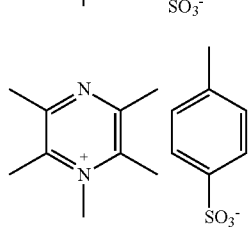
(Ex-6)

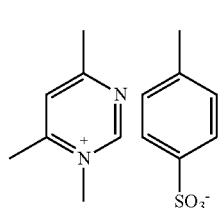
(Ex-7)

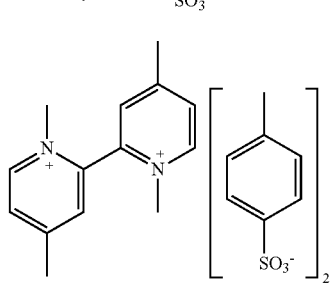
(Ex-8)

-continued (Ex-9)

[structure: bis(4-methylpyridinium)propane di(p-toluenesulfonate)]

The composition of the invention generally comprises salt (P) in an amount of at least 0.1, preferably at least 0.2, more preferably at least 0.3 weight part per 100 weight parts of fluoroelastomer (A) (phr).

The composition of the invention generally comprises salt (P) in an amount of at most 10, preferably at most 5, more preferably at most 3 weight parts per 100 weight parts of fluoroelastomer (A).

The base (B) suitable for being used in the composition (C) of the present invention is not particularly limited. One or more than one organic base, one or more than one inorganic base or mixtures of organic and inorganic base(s) (B) can be used.

Base (B) is preferably an inorganic base. Among inorganic bases [bases (IB)] mention can be notably made of:
  (i) divalent metal oxides, in particular oxides of alkali-earth metals or oxides of Zn, Mg, Pb, Ca, including specifically MgO, PbO and ZnO;
  (ii) hydroxides of metals, in particular hydroxides of monovalent and divalent metals, specifically hydroxides of alkali and alkali-earth metals, in particular hydroxides selected from the group consisting of $Ca(OH)_2$, $Sr(OH)_2$, and $Ba(OH)_2$;
  (iii) metal salts of weak acids having a $pK_a$ higher than 3, in particular weak acids selected from the group consisting of carbonates, benzoates, oxalates and phosphites; in particular Na, K, Ca, Sr, Ba salts of carbonates, benzoates, oxalates and phosphites.

Among inorganic bases, divalent metal oxides, in particular oxides of alkali-earth metals or oxides of Zn, Mg, Pb, Ca, including specifically MgO, PbO and ZnO, and more specifically, MgO, have been found to be particularly effective.

Mixtures of inorganic bases may be used; whereas more than one base (IB) are used, this plurality may be a combination of more than one divalent metal oxide (i), as detailed above, or may be a combination of one or more than one divalent metal oxide and of one or more than one hydroxide of metals (ii), as detailed above. A combination of MgO and $Ca(OH)_2$ is an exemplary embodiment of such combination.

Among organic based [bases (OB)] mention can be notably made of:
  (j) non-aromatic amines or amides complying with general formula (B1m) or (B1d):

$$R_{bm}-[C(O)]_t-NR^H_2 \quad (B1m)$$

$$R^H_2N-[C(O)]_{t'}-R_{dm}[C(O)]_{t''}-NR^H_2 \quad (B1d)$$

wherein:
  each of t, t' and t", equal to or different from each other and at each occurrence is zero or 1;
  each of $R^H$ is independently H or a $C_1$-$C_{12}$ hydrocarbon group;
  $R_{bm}$ is a monovalent hydrocarbon non-aromatic group having 1 to 30 carbon atoms;
  $R_{bm}$ is a divalent hydrocarbon non-aromatic group having 1 to 30 carbon atoms; and (jj) cycloaliphatic secondary or tertiary amines complying with general formula (B2m) or (B2d):

(B2m)

(B2d)

wherein:
  Cy represents a divalent aliphatic group comprising at least 4 carbon atoms, optionally comprising one or more than one ethylenically unsaturated double bond, and optionally comprising one or more catenary nitrogen atoms, forming a cycle with the nitrogen atom which is connected thereto;
  Cy' represent a trivalent aliphatic group comprising at least 5 carbon atoms, optionally comprising one or more than one ethylenically unsaturated double bond, and optionally comprising one or more catenary nitrogen atoms, forming a cycle with the nitrogen atom which is connected thereto;
  (jjj) aromatic amines or amides complying with general formula (B3):

$$Ar_b-\{[C(O)]_t-NR^H_2\}_w \quad (B3)$$

wherein:
  t, equal to or different from each other and at each occurrence, is zero or 1;
  w is an integer of 1 to 4;
  each of $R^H$ is independently H or a $C_1$-$C_{12}$ hydrocarbon group;
  $Ar_b$ is a mono- or poly-nuclear aromatic group, possibly comprising one or more than one catenary heteroatoms selected from the group consisting of S and O;
  (jv) heteroaromatic amines comprising at least one nitrogen atom comprised in a heteroaromatic cycle, in particular pyridine derivatives;
  (v) guanidine derivatives of formula (B4) or (B5):

(B4)

(B5)

wherein:
  each of $R^1$, $R^2$, $R^3$, $R^4$, $R^5$, $R^6$, $R^7$, and $R^8$, equal to or different from each other, is independently H or a $C_1$-$C_{12}$ hydrocarbon group and corresponding salts of said guanidines (B4) and (B5), in particular corresponding N-quaternized hydrohalides (preferably hydrochlorides);

(vj) metal alkoxylates, preferably alkoxylates of aliphatic alcohols.

Among bases of formulae (B1m) and (B1d), those wherein:
  $R_{bm}$ is a monovalent aliphatic linear group having 6 to 30 carbon atoms, possibly comprising one or more than one ethylenically unsaturated double bond; and
  $R_{dm}$ is a divalent aliphatic linear group having 6 to 30 carbon atoms, possibly comprising one or more than one ethylenically unsaturated double bond,
are particularly preferred.

Among the said non-aromatic amines or amides, mention can be particularly made of:
  octadecylamine of formula $CH_3(CH_2)_{17}$—$NH_2$;
  erucamide of formula $H_2N$—$C(O)$—$(CH_2)_{11}$—$CH$=$CH$—$(CH_2)_7CH_3$;
  oleamide of formula $H_2N$—$C(O)$—$(CH_2)_7$—$CH$=$CH$—$(CH_2)_7CH_3$;
  hexamethylenediamine of formula $H_2N$—$(CH_2)_6$—$NH_2$;
  N,N-dimethyloctylamine;
  N,N-dimethyldodecylamine;
  trioctylamine;
  trihexylamine.

Among the said cycloaliphatic secondary or tertiary amines, mention can be made of 1,8-diazabicycloundec-7-ene (DBU) of formula:

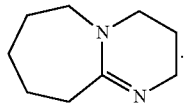 [SMILES: C1CCC2=NCCCN2CC1]

Exemplary embodiments of said guanidine derivatives of formula (B-4) are notably guanidine hydrochloride and di-o-tolylguanidine.

Exemplary embodiments of said metal alkoxylates are notably potassium terbutylate, sodium ethylate and sodium methylate.

Exemplary embodiments of said heteroaromatic amines are notably trimethylpyridine isomers.

While it is generally preferred for composition (C) to include at least one inorganic base, as detailed above, embodiments whereas composition (C) comprises at least one organic base, either in combination with one or more than one inorganic base, or without any inorganic base, are also within the scope of the present invention.

The amount of base (B) will be adjusted by one of ordinary skills in the art, taking into account the nature and basicity of base (B) used.

It is nevertheless understood that the composition (C) generally comprises from 0.2 to 25, preferably from 1 to 20 weight parts of said base (B) (organic and/or inorganic, as above detailed) per 100 weight parts of fluoroelastomer (A).

According to certain preferred embodiments, the composition (C) comprises at least one inorganic base, and more specifically at least one divalent metal oxide (i), as detailed above, in an amount of at least 2, preferably at least 3, more preferably at least 5 and/or of at most 18, preferably at most 17, more preferably at most 15 parts of said base (IB) per 100 weight parts of fluoroelastomer (A).

According to certain embodiments, the composition (C) comprises at least one organic base and at least one inorganic base. In these circumstances, the composition (C) generally comprises from 0.1 to 10, preferably from 6 to 16 weight parts of said inorganic base and/or generally, from 0.1 to 10, preferably from 6 to 16 weight parts of said organic base, these weight parts being referred to 100 weight parts of fluoroelastomer (A).

As said, the composition (C) comprises at least one polyhydroxylated compound. Aromatic or aliphatic polyhydroxylated compounds, or derivatives thereof, may be used; examples thereof are described, notably, in EP 335705 A (MINNESOTA MINING) 4 Oct. 1989 and U.S. Pat. No. 4,233,427 (RHONE POULENC IND) 11 Nov. 1980. Among these, mention will be made in particular of dihydroxy, trihydroxy and tetrahydroxy benzenes, naphthalenes or anthracenes; bisphenols of formula (B):

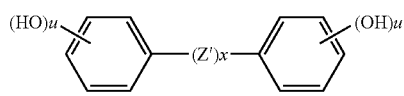

wherein:
  Z' is selected from the group consisting of bivalent $C_1$-$C_{13}$ alkyl or alkylidene group, $C_4$-$C_{13}$ cycloaliphatic, $C_6$-$C_{13}$ aromatic or arylalkylenic groups, optionally substituted with at least one chlorine or fluorine atom; a thio (—S—), oxy (—O—), carbonyl (—C(O)—), sulphinyl (—S(O)—) and sulphonyl group (—$SO_2$—);
  x is 0 or 1;
  u, equal to or different from each other, is independently at each occurrence an integer of at least 1, preferably 1 or 2;
  and wherein the phenyl rings can be optionally substituted by one or more substituents selected from the group consisting of chlorine, fluorine, bromine; —CHO, $C_1$-$C_8$ alkoxy groups, —$COOR_{10}$ groups, wherein $R_{10}$ is H or $C_1$-$C_8$ alkyl, $C_6$-$C_{14}$ aryl, $C_4$-$C_{12}$ cycloalkyl.

When Z' is a $C_1$-$C_{13}$ divalent alkyl group, it can be for example methylene, ethylene, chloroethylene, fluoroethylene, difluoroethylene, 1,3-propylene, tetramethylene, chlorotetramethylene, fluorotetramethylene, trifluorotetramethylene, 2-methyl-1,3-propylene, 2-methyl-1,2-propylene, pentamethylene, hexamethylene, hexafluoroisopropylidene.

When Z' is a $C_1$-$C_{13}$ divalent alkylidene group, it can be for example ethylidene, dichloroethylidene, difluoroethylidene, propylidene, isopropylidene, trifluoroisopropylidene, hexafluoroisopropylidene, butylidene, heptachlorobutylidene, heptafluorobutylidene, pentylidene, hexylidene, 1,1-cyclohexylidene.

When Z' is $C_4$-$C_{13}$ cycloaliphatic group, it can be for example 1,4-cyclohexylene, 2-chloro-1,4-cyclohexylene, 2-fluoro-1,4-cyclohexylene, 1,3-cyclohexylene, cyclopentylene, chlorocyclopentylene, fluorocyclopentylene, and cycloheptylene.

When Z' is a $C_6$-$C_{13}$ aromatic or arylalkylenic group, it can be for example m-phenylene, p-phenylene, 2-chloro-1,4-phenylene, 2-fluoro-1,4-phenylene, o-phenylene, methyl phenylene, dimethylphenylene, trimethylphenylene, tetramethyl phenylene, 1,4-naphthylene, 3-fluoro-1,4-naphthylene, 5-chloro-1,4-naphthylene, 1,5-naphtylene and 2,6-naphthylene.

Among dihydroxy benzenes, as mentioned above, the polyhydroxylated compounds may be selected from the group consisting of catechol, resorcinol, 2-methyl resorcinol, 5-methyl resorcinol, hydroquinone, 2-methyl hydroquinone, 2,5-dimethyl hydroquinone, 2-t-butyl hydroquinone.

Among dihydroxy naphthalenes, as mentioned above, the polyhydroxylated compounds may be selected from the group consisting of 1,5-dihydroxynaphthalene, 2,7-dihydroxynaphthalene, 1,7-dihydroxynaphthalene, 2,3-dihydroxynaphthalene, in particular, 1,5-dihydroxynaphthalene.

Among the polyhydroxylated compounds of formula (B), hexafluoroisopropylidene bis (4-hydroxybenzene), known as bisphenol AF, 4,4'-dihydroxydiphenyl sulphone and isopropylidene bis(4-hydroxybenzene), known as bisphenol A, are preferred, with bisphenol AF being particularly preferred.

It is also understood that derivatives of afore-mentioned polyhydroxylated compound can be used; mention can be notably made of metal salts formed by the corresponding anion of said polyhydroxylated compounds wherein one or more of the hydroxyl group has been deprotonated, with one or more than one cation (as required for reaching neutrality) of a metal, typically of an alkaline or alkaline earth metal; examples thereof are notably the di-potassic salt of bisphenol AF and the mono-sodic mono-potassic salt of bisphenol AF.

Further in addition, organic P, As, Se or S-onium salts, amino-phosphonium salts and diphosphine-iminium salts of hydroxylates of afore-mentioned polyhydroxylated compound can be used, i.e. salts formed by the anion of said polyhydroxylated compounds wherein one or more of the hydroxyl group has been deprotonated, with one or more cations used as accelerant (A) can also be used.

The amount of the polydroxylated compound is generally of at least 0.5 weight parts, preferably at least 1 weight parts, and/or generally at most 15 weight parts, preferably at most 10 weight parts, per 100 weight parts of fluoroelastomer (A).

The composition (C) comprises at least one accelerant selected from the group consisting of organic P, As, Se or S-onium compound, amino-phosphonium derivatives, phosphoranes, and diphosphine-iminium compounds.

Organic onium compounds which are suitable in the composition of the invention generally comply with formula (O):

$$\{[R^1R^2R^3R^4Q]^+\}_n X_I^{n-}$$

wherein:
Q is selected from the group consisting of phosphor, arsenic, antimony, sulphur; preferably phosphor;
$X_I$ is an organic or inorganic anion, preferably selected from the group consisting of halides, sulphate, acetate, phosphate, phosphonate, hydroxide, alkoxide, phenate, bisphenate;
n is the valence of the $X_I$ anion;
each of $R^2$, $R^3$, $R^4$, $R^5$, equal to or different from each other, is independently the one from the other selected from the group consisting of:
  a $C_1$-$C_{20}$ alkyl group, a $C_6$-$C_{20}$ aryl group, a $C_6$-$C_{20}$ arylalkyl group, a $C_1$-$C_{20}$ alkenyl group;
  a halogen selected from chlorine, fluorine, bromine;
  a cyano group, a group of formula —$OR_B$ or —$CO$-$OR_B$, wherein $R_B$ is an alkyl, aryl, arylalkyl or alkenyl; wherein two groups selected from $R^2$, $R^3$, $R^4$, $R^5$ may form with Q a cyclic structure;
  with the provisio that when Q is a sulphur atom one of the $R^2$, $R^3$, $R^4$, $R^5$ radicals is not present.

Amino-phosphonium derivatives which are suitable for use in composition (C) generally comply with formula (AP-1) or (AP-2):

  (AP-1)

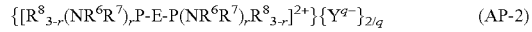  (AP-2)

wherein:
each of $R^6$, $R^7$ and $R^8$, equal to or different from each other, is independently selected from the group consisting of:
  $C_1$-$C_{18}$ alkyl group (preferably $C_1$-$C_{12}$ alkyl group); $C_4$-$C_7$ cycloalkyl group; $C_6$-$C_{18}$ aryl group (preferably $C_6$-$C_{12}$ aryl group); $C_6$-$C_{18}$ arylalkyl group (preferably $C_6$-$C_{12}$ arylalkyl group);
  $C_1$-$C_{18}$ oxyalkyl group comprising one or more than one hydroxyl or oxygen ethereal group;
and wherein $R^6$, $R^7$ and $R^8$ can optionally contain halogens, CN, OH, carbalkoxy groups; wherein $R^6$ and $R^7$ can form with the nitrogen atom an heterocyclic ring;
E is a $C_1$-$C_6$ divalent alkylenic, oxyalkylenic or $C_6$-$C_{12}$ arylenic radical;
n is an integer from 1 to 4;
r is an integer from 1 to 3;
q is the valence of the anion Y, and is preferably an integer from 1 to 2;
Y is an organic or inorganic anion having valence q; Y can be selected from halides, perchlorate, nitrate, tetrafluoroborate, hexafluorophosphate, oxalate, acetate, stearate, haloacetate, para-toluensulphonate, phenate, bisphenate, hydroxide; Y can also be a complex anion for example $ZnCl_4^{2-}$, $CdCl_4^{2-}$, $NiBr_4^{2-}$, $HgI_3^-$.

Phosphoranes which are suitable in the composition (C) generally comply with formula (P):

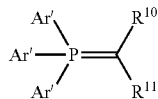

wherein:
each of Ar', equal to or different from each other, is a optionally substituted aryl group, preferably an optionally substituted phenyl group or an optionally substituted naphthyl group;
each of $R^{10}$ and $R^{11}$, equal to or different from each other, is independently selected from the group consisting of —H, —CN, $C_1$-$C_8$ alkyl, —O—C(O)—$R^{12}$ group, —C(O)—$R^{12}$ group, —$NR^{13}$—C(O)—$R^{12}$ group, with $R^{12}$ being a $C_1$-$C_6$ (cyclo)alkyl group, and $R^{13}$ being H or a $C_1$-$C_6$ (cyclo)alkyl group, $R^{10}$ and $R^{11}$ possibly forming together with the carbon atom of the P=C bond a cyclic group.

Diphosphine-iminium compounds which are suitable in the composition (C) generally comply with formula (I):

$$[(R^{14})_3P=N=P(R^{14})_3]^+\}_z X^{z-} \quad (I)$$

wherein:
$R^{14}$, equal to or different from each other at each occurrence, is selected from the group consisting of $C_1$-$C_{12}$ hydrocarbon groups, optionally comprising one or more than one group including a heteroatom selected from the group consisting of O, N, S, halogen;
X is an anion of valence z, with z being an integer, generally 1 or 2.

Examples of accelerants that may be used include: quaternary ammonium or phosphonium salts as notably described in EP 335705 A (MINNESOTA MINING) 4 Oct. 1989 and U.S. Pat. No. 3,876,654 (DUPONT) 8 Apr. 1975; aminophosphonium salts as notably described in U.S. Pat. No. 4,259,463 (MONTEDISON SPA) 31 Mar. 1981; phosphoranes as notably described in U.S. Pat. No. 3,752,787 (DUPONT) 14 Aug. 1973; diphosphine-iminium compounds as described in EP 0120462 A (MONTEDISON SPA) 3 Oct. 1984 or as described in EP 0182299 A (ASAHI CHEMICAL) 28 May 1986.

Quaternary phosphonium salts and aminophosphonium salts are preferred, and more preferably salts of tetrabutylphosphonium, of tetrabutyl ammonium, of 1,1-diphenyl-1-benzyl-N,N-diethyl-phosphoramine of formula:

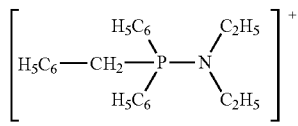

(in particular its chloride, also known as 1-chloro-N,N-diethyl-1,1-diphenyl-1(phenylmethyl) phosphoramine) and of benzyl(diethylamino)diphenylphosphanium of formula:

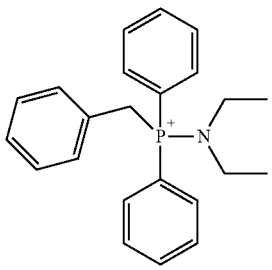

Instead of using the accelerator (A) and the polyhydroxylated compound separately, it is also possible to provide the same combined in composition (C) by mixing into the composition (C) adduct between an accelerant (A) and a polyhydroxylated compound in a mole ratio of from 1:2 to 1:5 and preferably from 1:3 to 1:5. In said adducts, the cation is hence represented by the positively charged moiety of any of the accelerants (A), in particular those selected from the group consisting of organic onium compounds, as detailed above, amino-phosphonium derivatives and imine compounds as listed above, and the anion is represented by the said polyhydroxylated compounds, wherein one or more of the hydroxyl group has been deprotonated.

The adducts between the accelerant (A) and the polyhydroxylated compound is generally obtained by melting a blend of the accelerant (A) and the polyhydroxylated compound in the indicated mole ratios, or by melting the mixture of the 1:1 adduct supplemented with an additional amount of the polyhydroxylated compound in the indicated amounts. Optionally, an excess of the accelerant (A), relative to that contained in the adduct, may also be present.

The following are particularly preferred as cations for the preparation of the adduct: 1,1-diphenyl-1-benzyl-N-diethylphosphoramine and tetrabutylphosphonium; particularly preferred anions are those derived from bisphenol compounds in which the two aromatic rings are bonded via a divalent radical chosen from perfluoroalkyl groups of 3 to 7 carbon atoms, and the OH groups are in the para position. A method suitable for the preparation of an adduct as above described is described in European patent application EP 0684277 A (AUSIMONT SPA) 29 Nov. 1995, which is included herein in its entirety by reference.

The composition (C) generally comprises the accelerant (A) in an amount of at least 0.05, preferably at least 0.1, more preferably at least 0.3 weight parts per 100 weight parts of fluoroelastomer (A), and/or generally of at most 8, preferably at most 5, more preferably at most 3 weight parts per 100 weight parts of fluoroelastomer (A).

Also, other conventional additives, such as reinforcing fillers (e.g. carbon black), thickeners, pigments, antioxidants, stabilizers and the like, may then be added to the composition (C).

Carbon black is among preferred reinforcing fillers. When used, reinforcing fillers, and more particularly carbon black, may be present in the composition (C) in an amount of at least 10, preferably at least 15, more preferably at least 20 weight parts; and/or at most 50, preferably at most 45, more preferably at most 40 weight parts per 100 weight parts of fluoroelastomer (A).

The invention also pertains to a method of using the composition (C), as above described, for fabricating shaped articles.

The composition (C) can be fabricated, e.g. by moulding (injection moulding, extrusion moulding), calendering, or extrusion, into the desired shaped article, which is advantageously subjected to vulcanization (curing) during the processing itself and/or in a subsequent step (post-treatment or post-cure), advantageously transforming the relatively soft, weak, fluoroelastomer (A) into a finished article made of non-tacky, strong, insoluble, chemically and thermally resistant cured fluoroelastomer.

Finally, the invention pertains to cured articles obtained from the composition (C), as above detailed.

The cured articles can be notably pipes, joints, O-ring, hose, and the like.

Should the disclosure of any of the patents, patent applications, and publications that are incorporated herein by reference conflict with the present description to the extent that it might render a term unclear, the present description shall take precedence.

The invention will be now described with reference to the following examples, whose purpose is merely illustrative and not intended to limit the scope of the invention.

EXAMPLES

Preparative Example
1—1,2,4,6-tetramethyl-pyridinium
p-toluenesulphonate of Formula (Ex-1)

A three-necked round bottom flask equipped with thermometer, condenser and stirring was charged with $CH_2Cl_2$ (85 ml) and methyl-p-toluenesulphonate (25.50 g). Then 2,4,6 trimethylpyridine (16.59 g) was added drop-wise at room temperature. The reaction was stirred at 50° C. and, after 22 hours, it was completed. The liquid phase was removed by evaporation under vacuum obtaining a white powder that was dispersed in diethyl-ether (50 ml) under stirring. The liquid phase was filtered off and 39.13 g of pure product was recovered as a white powder in 93% yield (melting point 161° C.; 1% weight loss: 266° C.).

$^1$H NMR (solvent D20, TMS reference): +7.70 ppm (d; 2H; ortho-H; p-toluenesulphonate); +7.55 (s; 2H; meta-H; 1,2,4,6-tetramethyl-pyridinium); +7.39 (d; $^2$H; meta-H; p-toluenesulphonate); +4.0 (s; 3H; $NCH_3$; 1,2,4,6-tetramethyl-pyridinium); +2.74 (s; 6H; ortho-$CH_3$; 1,2,4,6-tetramethyl-pyridinium); 2.53 (s; 3H; para-$CH_3$; 1,2,4,6-tetramethyl-pyridinium); +2.44 ppm (s; 3H; para-$CH_3$; p-toluenesulphonate).

General Compounding Procedure

The salts (P) of preparative example listed above were compounded between rolls to prepare curable compounds in combination with other ingredients, using as base fluoroelastomer resin a VDF-HFP copolymer commercially available under trade name TECNOFLON® N60HS from Solvay Specialty Polymers Italy S.p.A. (FKM-1, hereinafter).

GM102E phosphonium salt is 1-chloro-N,N-diethyl-1,1-diphenyl-1-(phenylmethyl)phosphoramine, supplied form Caffaro Industrie (GM 102E, hereinafter);

MAGLITE® DE high surface area, high activity magnesium oxide (Maglite® DE, herein after) was obtained from Merck;

Reinforcing filler Carbon black N990MT was obtained from Cancarb (NT990MT, hereinafter);

Bisphenol AF (or 2,2-bis-4-hydroxyphenyl)-hexafluoropropane) was supplied from Sigma Aldrich and used as received.

Characterization of Cure Behaviour

Cure behaviour was characterized by Moving Die Rheometer (MDR), at 170° C. or 190° C., by determining the following properties:

$M_L$=Minimum torque (lb×in)
$M_H$=Maximum torque (lb×in)
ts2 is scorch time, i.e. time required for torque to increase of two units from $M_L$; txx is the time required for reaching xx % of $M_H$.

O-rings (size class=214) have been molded and cured in a pressed mould comprising 12 cavities and then post-treated in an air circulating oven in conditions (time, temperature) below specified. Molding has been repeated 3 times for each recipe, so as to collect 36 O-ring specimens. The tensile properties have been determined on specimens punched out from the plaques, according to the ASTM D412C Standard at 23° C.

M 50 is the tensile strength in MPa at an elongation of 50%
M 100 is the tensile strength in MPa at an elongation of 100%
T.S. is the tensile strength in MPa;
E.B. is the elongation at break in %.

The Shore A hardness (3") (HDS) has been determined on 3 pieces of plaque piled according to the ASTM D 2240 method.

The compression set (C-SET) has been determined on O-ring specimen standard AS568A (type 214) or on 6 mm buttons (type 2), according to the ASTM D 395, method B, at 200° C. for 70 h.

Visual inspection of molded O-rings has been carried out and O-rings presenting no blisters on their surface were counted.

Results are summarized in tables below.

Table 1 compares the results obtained combining salt (P) of Ex. 1 with polyhydroxylated compound and accelerant (A), indicated above (see recipe of Ex. 2), with results obtained in the absence of salt (P) or in the absence of accelerant (A).

TABLE 1

| Ingredient | unit | Recipe A of comparison | Inventive Recipe | Recipe B of comparison |
|---|---|---|---|---|
| FKM-1 | phr | 100 | 100 | 100 |
| Bis-phenol AF | phr | 2.2 | 2.2 | 2.2 |
| GM102E | phr | 0.4 | 0.4 | 0 |
| Salt (P) Ex. 1 | phr | 0 | 0.5 | 1.05 |
| N990MT | phr | 30 | 30 | 30 |
| Maglite ® DE | phr | 7 | 7 | 7 |

TABLE 1-continued

| | | Curing behaviour | | |
|---|---|---|---|---|
| | unit | @170° C. | @170° C. | @190° C. |
| ML | lb*in | 1.0 | 1.1 | 1.1 |
| MH | lb*in | 10.5 | 17.7 | 17.8 |
| ts2 | sec | 165 | 58 | 267 |
| $t_{02}$ | sec | 67 | 30 | 127 |
| $t_{50}$ | sec | 221 | 183 | 902 |
| $t_{90}$ | sec | 375 | 463 | 2427 |
| $t_{95}$ | sec | 509 | 611 | 2891 |

Molding for $t_{90}$ at 170° C. and post-cure at 250° C. for 8 + 16 hours
Mechanical properties according to ASTM D4120 at 23° C.

| T.S. | MPa | 14.1 | 14.0 | 14.8 |
|---|---|---|---|---|
| M50 | MPa | 1.8 | 2.4 | 3.9 |
| M100 | MPa | 3.2 | 5.8 | 7.9 |
| E.B. | % | 272 | 181 | 161 |
| Hardness | Shore A | 64 | 68 | 77 |

Compression Set 70 hours at 200° C.

| C-Set | % | 16 | 25 | 36 |
|---|---|---|---|---|

Molding quality

| Blistered specimens | number | 36/36 | 4/36 | 5/36 |
|---|---|---|---|---|
| | % | 100 | 11 | 14 |

Data comprise above well demonstrate that the addition of salt (P) is effective in dramatically reducing the number of molded parts including blisters, while substantially maintaining same mechanical properties, and acceptable C-Set. When salt (P) is used in the absence of accelerant (A), despite the use of salt (P) in an increased amount and the adoption of higher curing temperature, the curing rate is absolutely unacceptable, although similar improvement in quality of molded parts is achieved, although with poorer C-set performances.

The invention claimed is:

1. A fluoroelastomer composition [composition (C)], said composition comprising:
   at least one vinylidene-fluoride based fluoroelastomer [fluoroelastomer (A)] comprising recurring units derived from vinylidene fluoride (VDF) and from at least one additional (per)fluorinated monomer different from VDF;
   at least one polyhydroxylated compound [compound (OH)];
   at least one basic compound [base (B)];
   at least one pyridinium salt [salt (P)] having an aromatic ring-quaternized nitrogen atom, and comprising at least two groups [groups (alpha-H)] having a carbon atom which bears at least a hydrogen atom and which is covalently bound to a $sp^2$-hybridized carbon of an annular aromatic carbon which is in ortho and/or para position to the said aromatic ring-quaternized nitrogen atom; and
   at least one accelerant [accelerant (A)], different from the at least one pyridinium salt [salt (P)], selected from the group consisting of organic P-onium compound, As-onium compound, Sb-onium compound, S-onium compound, amino-phosphonium derivatives, phosphoranes, and diphosphine-iminium compounds.

2. The composition of claim 1, wherein the at least one pyridinium salt [salt (P)] is selected from the group consisting of compounds complying with any of formulae (P1) to (12):

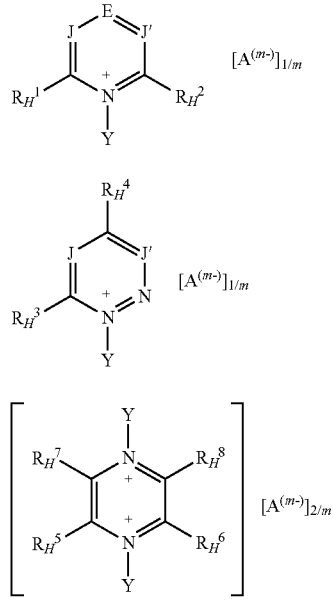 (P-1)

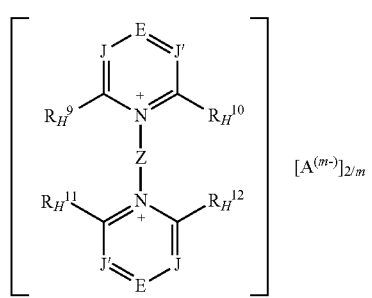 (P-2)

(P-3)

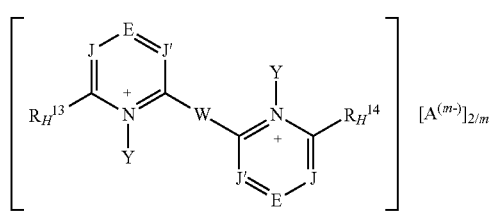 (P-4)

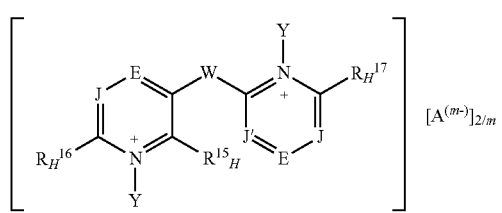 (P-5)

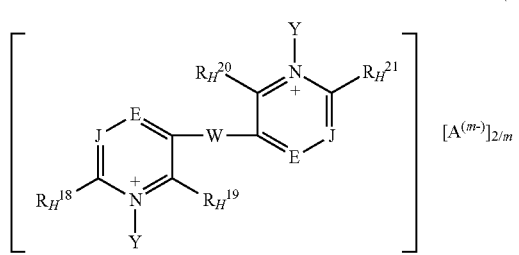 (P-6)

(P-7)

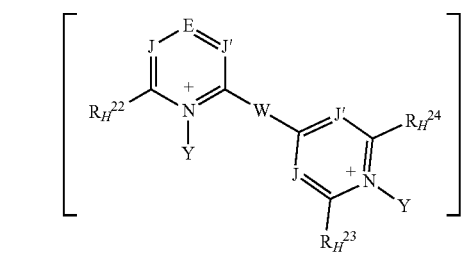 (P-8)

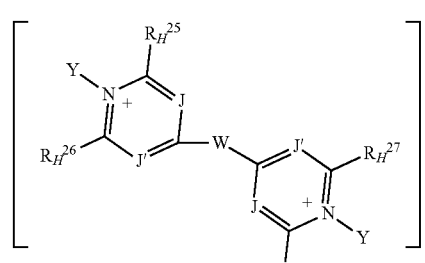 (P-9)

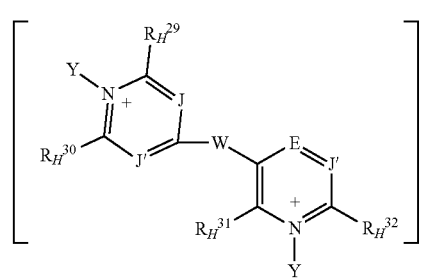 (P-10)

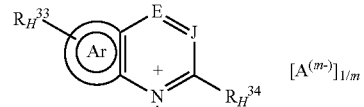 (P-11)

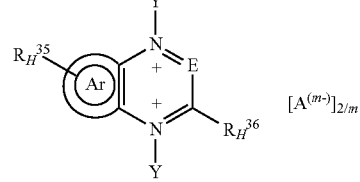 (P-12)

wherein:
each of J and J', equal to or different from each other, is independently at each occurrence C—R* or N, wherein R* is H or a $C_1$-$C_{12}$ hydrocarbon group;

E is N or a group of formula C—R°$_H$;

Z is a divalent hydrocarbon group having from 1 to 12 carbon atoms;

W is a bond or is a bridging group selected from the group consisting of divalent hydrocarbon groups having from 1 to 12 carbon atoms and divalent fluorocarbon groups having from 1 to 12 carbon atoms;

the group sketched with symbol:

in formula (P-11) and (P-12) designates an aromatic mono- or poly-nuclear ring condensed to the pyridinium aromatic ring, which may include one or more additional nitrogen atoms, optionally quaternized nitrogen atoms, in the ring(s);

each of $R^1_H$, $R^2_H$, $R^3_H$, $R^4_H$, $R^5_H$, $R^6_H$, $R^7_H$, $R^8_H$, $R^9_H$, $R^{10}_H$, $R^{11}_H$, $R^{12}_H$, $R^{13}_H$, $R^{14}_H$, $R^{15}_H$, $R^{16}_H$, $R^{17}_H$, $R^{18}_H$, $R^{19}_H$, $R^{20}_H$, $R^{21}_H$, $R^{22}_H$, $R^{23}_H$, $R^{24}_H$, $R^{25}_H$, $R^{26}_H$, $R^{27}_H$, $R^{28}_H$, $R^{29}_H$, $R^{30}_H$, $R^{31}_H$, $R^{32}_H$, $R^{33}_H$, $R^{34}_H$, $R^{35}_H$, $R^{36}_H$ and $R^o_H$, equal to or different from each other, is independently at each occurrence —H or a group of formula [group (alpha-H)]:

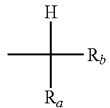

wherein $R_a$, and $R_b$, equal to or different from each other, are independently H or a hydrocarbon $C_1$-$C_6$ group;

Y, equal to or different from each other, is independently oxygen or a $C_1$-$C_{12}$ hydrocarbon group, which is an aliphatic or an aromatic group, which optionally has one or more than one heteroatoms selected from N, O, S and halogens; and $A^{(m-)}$ is an anion having valency with the proviso that (i) when salt (P) is of formula (P-1) each of $R^1_H$ and $R^2_H$, are groups (alpha-H);

(ii) when salt (P) is of formula (P-2) $R^3_H$ and $R^4_H$ are groups (alpha-H);

(iii) when salt (P) is of formula (P-3), at least two of $R^5_H$, $R^6_H$, $R^7_H$, and $R^8_H$ are groups (alpha-H);

(iv) when salt (P) is of formula (P-4), at least two of $R^9_H$, $R^{10}_H$, $R^{11}_H$, $R^{12}_H$, and $R^oH$ are groups (alpha-H);

(v) when salt (P) is of formula (P-5), at least two of $R^3_H$, $R^4_H$, and $R^o_H$ are groups (alpha-H);

(vi) when salt (P) is of formula (P-6), at least two of $R^{15}_H$, $R^{16}_H$, $R^{17}_H$, and $R^o_H$ are groups (alpha-H);

(vii) when salt (P) is of formula (P-7), at least two of $R^{18}_H$, $R^{19}_H$, $R^{20}_H$, $R^{21}_H$, and $R^oH$ are groups (alpha-H);

(viii) when salt (P) is of formula (P-8), at least two of $R^{22}_H$, $R^{23}_H$, $R^{24}_H$, and $R^o_H$ are groups (alpha-H);

(ix) when salt (P) is of formula (P-9), at least two of $R^{25}_H$, $R^{26}_H$, $R^{27}_H$, and $R^{28}_H$ are groups (alpha-H);

(x) when salt (P) is of formula (P-10), at least two of $R^{29}_H$, $R^{30}_H$, $R^{31}_H$, $R^{32}_H$, and $R^o_H$ are groups (alpha-H);

(xi) when salt (P) is of formula (P-11), at least two of $R^{33}_H$, $R^{34}_H$, and $R^o_H$ are groups (alpha-H); and (xii) when salt (P) is of formula (P-12), at least two of $R^{35}_H$, $R^{36}_H$ and $R^o_H$ are groups (alpha-H).

3. The composition (C) of claim 2, (1) wherein salts (P) of formula (P-1) are those complying with formulae (P-1-a) to (P-1-e):

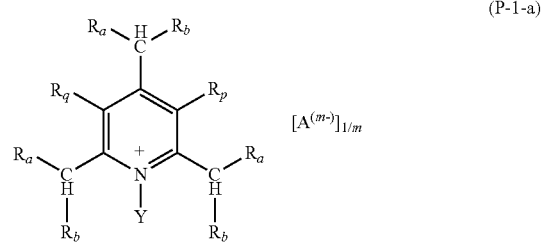

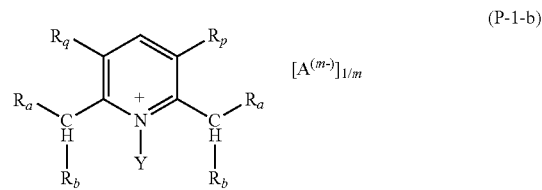

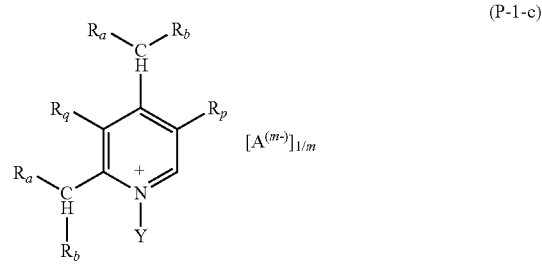

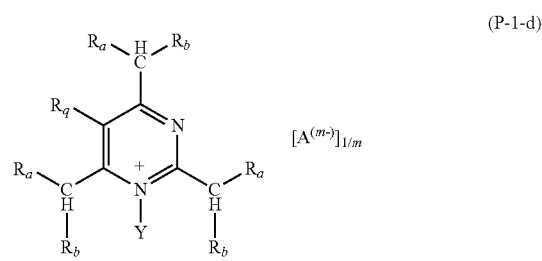

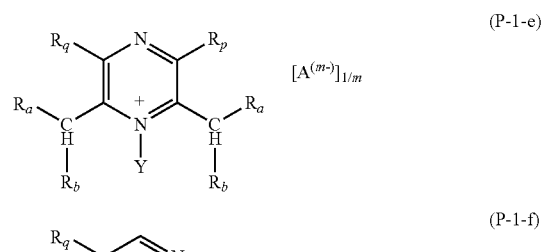

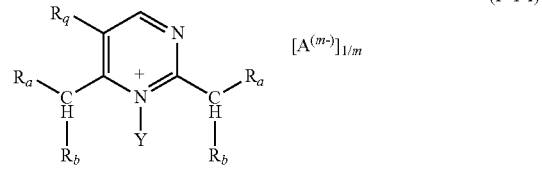

wherein:

$R_a$ and $R_b$ have the meaning as defined in claim 2;

Y has the meaning as defined in claim 2;

each of $R_p$ and $R_q$, equal to or different from each other, is H or a $C_1$-$C_{12}$ hydrocarbon group;

A and m have the meanings as defined in claim 2; and/or (2) wherein salts (P) of formula (P-2) are those complying with formula (P-2-a):

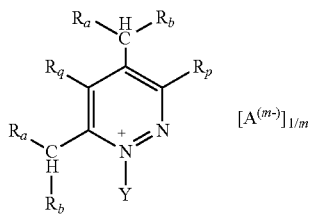

(P-2-a)

wherein:
- $R_a$ and $R_b$ have the meaning as defined in claim 2;
- Y has the meaning as defined in claim 2;
- each of $R_p$ and $R_q$, equal to or different from each other, is H or a $C_1$-$C_{12}$ hydrocarbon group;
- A and m have the meanings as defined in claim 2;

and/or (3) wherein salts (P) of formula (P-3) are those complying with formula (P-3-a):

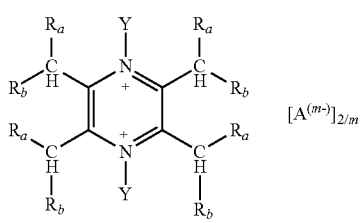

(P-3-a)

wherein:
- $R_a$ and $R_b$ have the meaning as defined in claim 2;
- Y has the meaning as defined in claim 2;
- A and m have the meanings as defined in claim 2;

and/or (4) wherein salts (P) of formula (P-4) are those complying with formula (P-4-a):

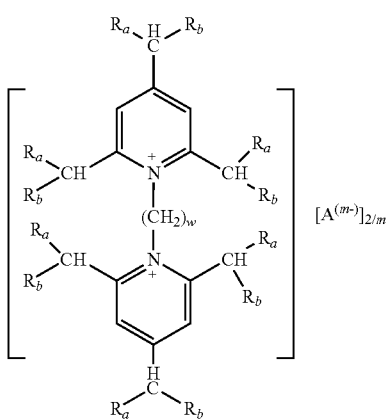

(P-4-a)

wherein:
- $R_a$ and $R_b$ have the meaning as defined in claim 2;
- w is an integer of 1 to 12;
- A and m have the meanings as defined in claim 2;

and/or (5) wherein salts (P) of formula (P-5) are those complying with formula (P-5-a):

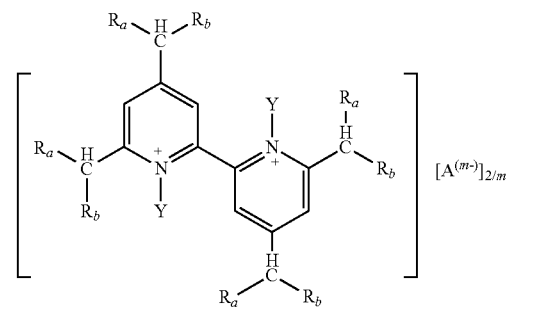

(P-5-a)

wherein:
- $R_a$ and $R_b$ have the meaning as defined in claim 2;
- Y has the meaning as defined in claim 2;
- A and m have the meanings as defined in claim 2;

and/or (6) wherein salts (P) of formula (P-11) are those complying with formula (P-11-a):

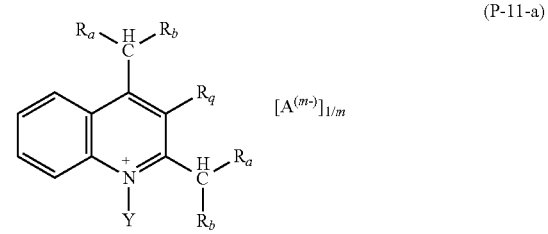

(P-11-a)

wherein:
- $R_a$ and $R_b$ have the meaning as defined in claim 2;
- Y has the meaning as defined in claim 2;
- A and m have the meanings as defined in claim 2;

and/or (7) wherein salts (P) of formula (P-12) are those complying with formula (P-12-a):

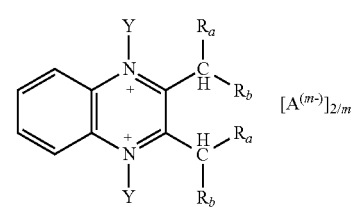

(P-12-a)

wherein:
- $R_a$ and $R_b$ have the meaning as defined in claim 2;
- Y has the meaning as defined in claim 2;
- A and m have the meanings as defined in claim 2.

4. The composition (C) of claim 1, wherein the at least one basic compound [base (B)] is an inorganic base selected from the group consisting of:
 i) divalent metal oxides
 ii) hydroxides of metals, and
 iii) metal salts of weak acids having a $pK_a$ higher than 3.

5. The composition (C) of claim 1, wherein the at least one basic compound [base (B)] is an organic base selected from the group consisting of:

(j) non-aromatics complying with general formula (B1m), non-aromatics complying with general formula (B1d):

$$R_{bm}\text{—}[C(O)]_t\text{—}NR^H_2 \tag{B1m}$$

$$R^H_2N\text{—}[C(O)]_t\text{—}R_{dm}\text{—}[C(O)]_{t''}\text{—}NR^H_2 \tag{B1d}$$

wherein:
  each of t, t' and t", equal to or different from each other and at each occurrence is zero or 1;
  each of RH is independently H or a $C_1$-$C_{12}$ hydrocarbon group;
  $R_{bm}$ is a monovalent hydrocarbon non-aromatic group having 1 to 30 carbon atoms;
  $R_{dm}$ is a divalent hydrocarbon non-aromatic group having 1 to 30 carbon atoms;
(jj) cycloaliphatic secondary amines complying with general formula (B2m), cycloaliphatic tertiary amines complying with general formula (B2d):

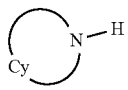

(B2m)

(B2d)

wherein:
  Cy represents a divalent aliphatic group having at least 4 carbon atoms, optionally having one or more than one ethylenically unsaturated double bond, and optionally having one or more catenary nitrogen atoms, forming a cycle with the nitrogen atom which is connected thereto;
  Cy' represent a trivalent aliphatic group having at least 5 carbon atoms, optionally having one or more than one ethylenically unsaturated double bond, and optionally having one or more catenary nitrogen atoms, forming a cycle with the nitrogen atom which is connected thereto;
(jjj) aromatics complying with general formula (B3):

$$Ar_b\text{—}\{[C(O)]_t\text{—}NR^H_2\}_w \tag{B3}$$

wherein:
  t, equal to or different from each other and at each occurrence, is zero or 1;
  w is an integer of 1 to 4;
  each of $R^H$ is independently H or a $C_1$-$C_{12}$ hydrocarbon group;
  $Ar_b$ is a mono- or poly-nuclear aromatic group, optionally having one or more than one catenary heteroatoms selected from the group consisting of S and O;
(jv) heteroaromatic amines having at least one nitrogen atom in the heteroaromatic cycle;
(v) guanidine derivatives of formula (B4), guanidine derivatives of formula (B 5):

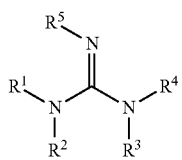

(B4)

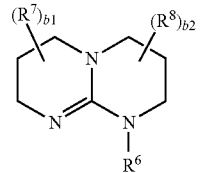

(B5)

wherein:
  each of $R^1$, $R^2$, $R^3$, $R^4$, $R^5$, $R^6$, $R^7$, and $R^8$, is independently H or a $C_1$-$C_{12}$ hydrocarbon group
  and corresponding salts of said guanidines (B4) and (B5); and
(vj) metal alkoxylates.

6. The composition (C) according to claim 1, wherein said at least one polyhydroxylated compound [compound (OH)] is selected from the group consisting of:
  dihydroxy, trihydroxy and tetrahydroxy benzenes, naphthalenes, and anthracenes; and
  bisphenols of formula (B):

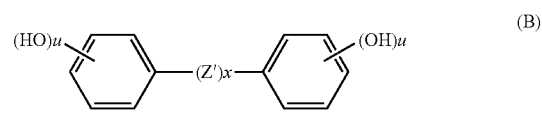

(B)

wherein:
  Z' is selected from the group consisting of bivalent $C_1$-$C_{13}$ alkyl or alkylidene group, $C_4$-$C_{13}$ cycloaliphatic, $C_6$-$C_{13}$ aromatic or arylalkylenic groups, optionally substituted with at least one chlorine or fluorine atom; a thio (—S—), oxy (—O—), carbonyl (—C(O)—), sulphinyl (—S(O)—) and sulphonyl group (—$SO_2$—);
  x is 0 or 1;
  u, equal to or different from each other, is independently at each occurrence an integer of at least 1 and no more than 5;
  and wherein the phenyl rings optionally are substituted by one or more substituents selected from the group consisting of chlorine, fluorine, bromine; —CHO, $C_1$-$C_8$ alkoxy groups, —$COOR_{10}$ groups, wherein Rio is H or $C_1$-$C_8$ alkyl, $C_6$-$C_{14}$ aryl, and $C_4$-$C_{12}$ cycloalkyl.

7. The composition (C) according to claim 1 wherein the at least one accelerant [accelerant (A)] is selected from the group consisting of:
  —P-onium, As-onium, Sb-onium and S-onium compounds complying with formula (O):

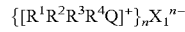

wherein:
  Q is selected from the group consisting of phosphor, arsenic, antimony, and sulphur;
  $X_I$ is an organic or inorganic anion, selected from the group consisting of halides, sulphate, acetate, phosphate, phosphonate, hydroxide, alkoxide, phenate, and bisphenate;
  n is the valence of the $X_I$ anion;
  each of $R^1$, $R^2$, $R^3$, $R^4$, is independently selected from the group consisting of:
    a $C_1$-$C_{20}$ alkyl group, a $C_6$-$C_{20}$ aryl group, a $C_6$-$C_{20}$ arylalkyl group, a $C_1$-$C_{20}$ alkenyl group;
    chlorine, fluorine, bromine;

a cyano group, —$OR_B$ and —$COOR_B$, wherein $R_B$ is an alkyl, aryl, arylalkyl or alkenyl; wherein two groups selected from $R^1$, $R^2$, $R^3$, $R^4$, optionally forms with Q a cyclic structure;
with the provisio that when Q is a sulphur atom one of the $R^1$, $R^2$, $R^3$, $R^4$, radicals is not present;
amino-phosphonium derivatives complying with formula (AP-1), amino-phosphonium derivatives complying with formula (AP-2):

  (AP-1)

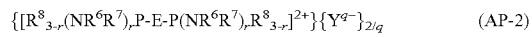  (AP-2)

wherein:
each of $R^6$, $R^7$ and $R^8$ is independently selected from the group consisting of:
$C_1$-$C_{18}$ alkyl group; $C_4$-$C_7$ cycloalkyl group; $C_6$-$C_{18}$ aryl group; $C_6$-$C_{18}$ arylalkyl group; and
$C_1$-$C_{18}$ oxyalkyl group having one or more than one hydroxyl or oxygen ethereal group;
and wherein $R^6$, $R^7$ and $R^8$ optionally contains halogens, CN, OH, carbalkoxy groups;
wherein $R^6$ and $R^7$ optionally forms with the nitrogen atom an heterocyclic ring;
E is a $C_1$-$C_6$ divalent alkylenic, oxyalkylenic or $C_6$-$C_{12}$ arylenic radical;
n is an integer from 1 to 4;
r is an integer from 1 to 3;
q is the valence of the anion Y;
Y is an organic or inorganic anion having valence q;
phosphoranes complying with formula (P):

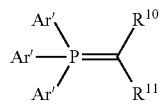

wherein:
each of Ar', equal to or different from each other, is an optionally substituted aryl group;
each of $R^{10}$ and $R^{11}$, is independently selected from the group consisting of —H, —CN, $C_1$-$C_8$ alkyl, —O—C(O)—$R^{12}$ group, —C(O)—$R^{12}$ group, and —$NR^{13}$—C(O)—$R^{12}$ group, with $R^{12}$ being a $C_1$-$C_6$ (cyclo)alkyl group, and $R^{13}$ being H or a $C_1$-$C_6$ (cyclo)alkyl group,
$R^{10}$ and $R^{11}$ possibly optionally forming together with the carbon atom of the P=C bond a cyclic group; and
diphosphine-iminium compounds complying with formula (I):

  (I)

wherein:
$R^{14}$, equal to or different from each other at each occurrence, is selected from the group consisting of $C_1$-$C_{12}$ hydrocarbon groups, optionally having one or more than one group including a heteroatom selected from the group consisting of O, N, S, and halogen; and
X is an anion of valence z, with z being an integer of 1 or 2.

8. The composition (C) according to claim 1, wherein the fluoroelastomer (A) comprises at least 15% moles, with respect to all recurring units of the fluoroelastomer (A), and/or wherein the fluoroelastomer (A) comprises at most 85% moles of recurring units derived from VDF, with respect to all recurring units of the fluoroelastomer.

9. The composition (C) of claim 1, wherein said at least one additional (per)fluorinated monomer different from VDF is selected from the group consisting of:
(a) $C_2$-$C_8$ perfluoroolefins;
(b) hydrogen-containing $C_2$-$C_8$ olefins different from VDF;
(c) $C_2$-$C_8$ chloro bromo iodo-fluoroolefins;
(d) (per)fluoroalkylvinylethers (PAVE) of formula $CF_2$=$CFOR_f$, wherein $R_f$ is a $C_1$-$C_6$ (per) fluoroalkyl group;
(e) (per)fluoro-oxy-alkylvinylethers of formula $CF_2$=CFOX, wherein X is a $C_1$-$C_{12}$ ((per) fluoro)-oxyalkyl comprising having catenary oxygen atoms;
(f) (per)fluorodioxoles having formula:

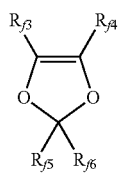

wherein each of $R_{f3}$, $R_{f4}$, $R_{f5}$, $R_{f6}$, is independently a fluorine atom, a $C_1$-$C_6$ fluoro- or per(halo)fluoroalkyl, optionally having one or more oxygen atom; and
(g) (per)fluoro-methoxy-vinylethers having formula:

wherein $R''_f$ is selected among $C_1$-$C_6$ (per)fluoroalkyls, linear or branched; $C_5$-$C_6$ cyclic (per)fluoroalkyls; and $C_2$-$C_6$ (per)fluorooxyalkyls, linear or branched, having from 1 to 3 catenary oxygen atoms, and $X_2$=F or H.

10. The composition according to claim 1, wherein fluoroelastomer (A) is selected from the group consisting of fluoroelastomers having the following monomer compositions (in mol %):
(i) vinylidene fluoride (VDF) 35-85%, hexafluoropropene (HFP) 10-45%, tetrafluoroethylene (TFE) 0-30%, perfluoroalkyl vinyl ethers (PAVE) 0-15%, bis-olefin (OF) 0-5%;
(ii) vinylidene fluoride (VDF) 50-80%, perfluoroalkyl vinyl ethers (PAVE) 5-50%, tetrafluoroethylene (TFE) 0-20%, bis-olefin (OF) 0-5%;
(iii) vinylidene fluoride (VDF) 20-30%, $C_2$-$C_8$ non-fluorinated olefins (O1) 10-30%, hexafluoropropene (HFP) and/or perfluoroalkyl vinyl ethers (PAVE) 18-27%, tetrafluoroethylene (TFE) 10-30%, bis-olefin (OF) 0-5%;
(iv) tetrafluoroethylene (TFE) 33-75%, perfluoroalkyl vinyl ethers (PAVE) 15-45%, vinylidene fluoride (VDF) 5-30%, hexafluoropropene HFP 0-30%, bis-olefin (OF) 0-5%; and
(v) vinylidene fluoride (VDF) 35-85%, fluorovinyl ethers (MOVE) 5-40%, perfluoroalkyl vinyl ethers (PAVE) 0-30%, tetrafluoroethylene (TFE) 0-40%, hexafluoropropene (HFP) 0-30%, bis-olefin (OF) 0-5%.

11. The composition (C) according to claim 1, wherein:
the composition comprises the at least one pyridinium salt [salt (P)] in an amount of at least 0.1 part per 100 weight parts of fluoroelastomer (A) (phr); and/or in an amount of at most 10 weight parts per 100 weight parts of fluoroelastomer (A); and/or the composition (C) comprises the at least one basic compound [base (B)] in an amount of at least 0.2 per 100 weight parts of fluoroelastomer (A) (phr); and/or in an amount of at most 25 per 100 weight parts of fluoroelastomer (A); and/or the composition (C) comprises the polyhydroxylated compound [compound (OH)] in an amount of at least 0.5 weight parts, and/or at most 15 weight parts per 100 weight parts of fluoroelastomer (A); and/or the composition (C) comprises the at least one accelerant [accelerant (A)] in an amount of at least 0.05 weight parts per 100 weight parts of fluoroelastomer (A), and/or of at most 8 weight parts per 100 weight parts of fluoroelastomer (A).

12. The composition (C) according to claim 1, said composition further comprising at least one reinforcing filler in an amount of at least 10; and/or at most 50 parts per 100 weight parts of fluoroelastomer (A).

13. A method for fabricating shaped articles, comprising using the composition (C) of claim 1.

14. Cured articles obtained from the composition (C) of claim 1.

* * * * *